(12) United States Patent
Steffes

(10) Patent No.: US 6,442,410 B1
(45) Date of Patent: Aug. 27, 2002

(54) NON-INVASIVE BLOOD GLUCOSE MEASUREMENT SYSTEM AND METHOD USING OPTICAL REFRACTOMETRY

(75) Inventor: Paul G. Steffes, Norcross, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 5 days.

(21) Appl. No.: 09/590,495

(22) Filed: Jun. 9, 2000

Related U.S. Application Data

(60) Provisional application No. 60/138,465, filed on Jun. 10, 1999.

(51) Int. Cl.[7] .................................................. A61B 5/00
(52) U.S. Cl. ........................ 600/319; 600/322; 600/316
(58) Field of Search ................................ 600/309–310, 600/318, 316, 319, 322–326

(56) References Cited

U.S. PATENT DOCUMENTS

| | | | |
|---|---|---|---|
| 3,802,777 A | | 4/1974 | Regnier et al. |
| 3,958,560 A | | 5/1976 | March |
| 3,963,019 A | * | 6/1976 | Quandt ........................ 600/319 |
| 4,014,321 A | | 3/1977 | March |
| 4,620,284 A | | 10/1986 | Schnell et al. |
| 4,648,714 A | | 3/1987 | Benner et al. |
| 4,676,639 A | | 6/1987 | Van Wagenen |
| 4,704,029 A | * | 11/1987 | Van Heuvelen ............... 356/39 |
| 4,758,081 A | | 7/1988 | Barnes |
| 4,832,483 A | | 5/1989 | Verma |
| 5,243,983 A | | 9/1993 | Tarr et al. |
| 5,433,197 A | * | 7/1995 | Stark .......................... 600/319 |
| 5,713,353 A | * | 2/1998 | Castano ...................... 600/319 |
| 6,152,875 A | * | 11/2000 | Hakamata .................... 600/319 |
| 6,259,937 B1 | * | 6/2001 | Schulman et al. .......... 600/345 |

OTHER PUBLICATIONS

Webster's II New Riverside University Dictionary, The Riverside Publishing Company, 1994, p. 988.*

* cited by examiner

*Primary Examiner*—Eric F. Winakur
*Assistant Examiner*—Matthew Kremer
(74) *Attorney, Agent, or Firm*—Todd Deveau; Charles Vorndran; Troutman Sanders LLP

(57) ABSTRACT

A method for determining blood glucose levels by measuring the glucose concentration in the ocular aqueous humor using optical refractometry by passing laser light the aqueous ocular humor, measuring the laser light's optical refractivity, and comparing the refractivity with known data, the comparison yielding the blood glucose level.

17 Claims, 5 Drawing Sheets

$t_k = (y_{k+1} - y_k)/u_k$
$C_k = 1/R_k$
$y_{k+1} = y_k + u_k t_k$
$nu_{k+1} = nu_k - y_{k+1}(n_{k+1} - n_k) C_{k+1}$
$u_k = u_{k+1}/-t_k$

NON-INVASIVE BLOOD GLUCOSE MEASUREMENT SYSTEM AND METHOD USING OPTICAL REFRACTOMETRY

This application claims the benefit of U.S. provisional application No. 60/138,465 filed Jun. 10, 1999.

FIELD OF THE INVENTION

The invention relates generally to the field of measuring the blood glucose levels of humans and, more specifically, to the field of measuring the blood glucose levels of humans using non-invasive techniques by measuring the optical refractivity of the ocular aqueous humor and comparing the measurements to known data.

BACKGROUND OF THE INVENTION

The potential for the non-invasive measurement of blood glucose concentration to improve the level of blood sugar control and the quality of life of diabetic patents has been recognized for nearly three decades. Cahill, G. F. et al, Practical Developments in Diabetes Research, *Diabetes* Vol. 21 (Supp. 2), pp. 703–712 (1972). However, the ability to realize highly reliable and robust instrumentation capable of such measurements has continued to prove an elusive goal.

The common thread among nearly all non-invasive techniques is the use of electromagnetic radiation to measure directly, or to infer indirectly, the blood glucose concentration. Numerous attempts have been made at non-invasive glucose measurement by directing electromagnetic radiation through the skin to measure blood glucose directly.

The most promising direct measurement approaches transmit radiation in the near infrared portion of the electromagnetic spectrum through the skin and estimate glucose concentration from the spectral signature of the absorption at selected wavelengths from 1–3 microns. In the 1–3 micron range, the absorption spectrum from water is not as dominant as at longer wavelengths, and there exist a number of unique, detectable features in the glucose absorption spectrum. Arnold, M. A., *Handbook of Clinical Laboratory Automation, Robotics and Optimization*, Chapter 26 (ed. Kost), John Wiley & Sons, New York (1996); Burmeister, J. J. et al., Spectroscopic Considerations for Noninvasive Blood Glucose Measurements with Near Infrared Spectroscopy, *IEEE LEOS Newsletter*, Vol. 12, pp. 6–9 (1998). However, transdermal measurements are especially challenging given the variability in path length from measurement to measurement, and given the spectral complexity of the fatty tissue and the myriad of constituents contained in biofluids such as whole blood. Approaches for correcting for such effects are discussed by Burmeister and Arnold.

As an alternative, the ocular aqueous humor (in the anterior portion of the eye) contains far fewer constituents that would interfere with the spectroscopic detection of glucose. Lambert, J. et al., Measurement of Physiologic Glucose Levels Using Raman Spectroscopy in a Rabbit Aqueous Humor Model, *IEEE LEOS Newsletter*, Vol. 12, pp. 19–22 (1998); Wicksted, J. P. et al., Raman Spectroscopy Studies of Metabolic Concentrations in Aqueous Solutions and Aqueous Humor Specimens, *Applied Spectroscopy*, Vol. 49, pp. 987–993 (1995). Likewise, if the eye position can be held stable relative to the sensor, the path length through the anterior portions of the eye is quite stable.

Throughout the 1950's and 60's, a number of studies of the relationship between blood glucose levels and glucose levels in the aqueous humor were conducted. Kinsey, V. E. et al., Transport of Glucose Across Blood-Aqueous Barriers as Affected by Insulin, *Journal of Physiology*, Vol. 156, pp. 8–16 (1961); Pohoja, S., The Steady-State Ratio of Aqueous Glucose in Diabetic Hyperglycemia, *Acta Ophthalmologica* [*Supp.*], Vol. 88, pp. 51–54 (1966). In vivo measurements showed a steady-state ratio of blood plasma glucose levels to aqueous humor levels of 1.05 in rabbits, and a ratio of approximately 1.8 for the two human patients tested. Reim, M. et al., Steady State Levels of Glucose in the Different Layers of the Cornea, Aqueous Humor, Blood and Tears In Vivo, *Ophthalmologica*, Vol. 154, pp. 39–50 (1967). This corresponds to a ratio of steady-state whole blood glucose concentration to aqueous ocular glucose concentration of approximately 1.6. Moreover, variations in blood glucose levels are reflected in corresponding variations in the concentration in the aqueous humor. Pohoja, S., The Glucose Content of the Aqueous Humor in Man, *Dissertation*, University of Helsinki (1966).

In the nearly three decades since Cahill et al, supra, suggested that some property such as refractive index or near-infrared absorbance could be measured and correlated with glucose level, a wide range of optical techniques have been promoted for determination of the glucose concentration in the aqueous humor. In U.S. Pat. No. 3,958,560 to March, use of a contact lens with an integrated infrared source, such as zirconium-filament light bulb, and a detector which would measure the amount of energy transmitted transversally through the cornea anterior to the iris and pupil is disclosed. In such a system, the enhanced absorption from the hydroxyl portion of the glucose molecule was thought to be measurable, and would be directly proportional to glucose abundance. March '560 also suggested that visible light might be introduced on the same transversal path and detected by an interferometer, which would measure the change in refractive index due to the refraction from glucose in the aqueous humor. The change in refractive index would likewise be proportional to glucose concentration in the aqueous humor. Unfortunately, neither effect was shown to be measurable using the technological approaches of the 1970's.

As an alternative, in U.S. Pat. No. 4,014,321 to March, a system which radiated polarized light on the transversal path through the cornea and then measured the change in polarization upon exit could be used to infer the glucose concentration in the aqueous humor since glucose is optically active is disclosed. This was especially attractive, since the majority of laser energy would not be directed toward the retina. The safe retinal exposure level for pulsed lasers in the near IR is on the order of 1–10 millijoules depending on pulse duration, with an exposure power limit of approximately to microwatts for continuous wave (CW) exposure. FDA Standards for Laser Safety, 21 C.F.R. Sec. 1040; Tarr, R. V. et al., The Non-Invasive Measure of D-Glucose in the Ocular Aqueous Humor using Stimulated Raman Spectroscopy, *IEEE LEOS Newsletter*, Vol. 12, pp. 22–27 (1998).

The use of optical polarimetry for measurement of ocular glucose has been a dynamic area of research of the past two decades. Results were reported from tests of an optical bench model of a polarimetric glucose sensor in which glucose concentrations as low 20 mg/dl were measured in a test cell. Rabinovitch, B. et al., Noninvasive Glucose Monitoring of the Aqueous Humor of the Eye: Part I. Measurement of Very Small Optical Rotations, *Diabetes Care*, Vol. 5, pp. 254–258 (1982). This corresponded to optical rotations of about only 40 arcseconds. The same optical bench model was used to measure glucose concentrations of rabbit ocular aqueous humor which was removed by paracentesis directly into a test cell. March, W. F. et al., Noninvasive Glucose Monitoring of the Aqueous humor of the Eye: Part II. Animal Studies and the Scleral Lens, *Diabetes Care*, Vol. 5, pp. 259–265 (1982). Work on an experimental scleral lens was also described in this study for non-invasive measurement of glucose concentrations in the aqueous humor of test animals, but the optical activity of constituents other than glucose, plus the birefringence of the cornea, made it extremely difficult to unambiguously infer the glucose concentration in the aqueous humor of the test animals.

In an attempt to correct for these problems, a multi-wavelength polarimeter, which has the potential to detect possible wavelength dependencies in the optical activity, which could then make it possible to separate the effects of the different constituents and to correct for birefringence in the cornea has been suggested. McNichols, R. J. et al., Development of a Non-Invasive Polarimetric Glucose Sensor, *IEEE LEOS Newsletter*, Vol. 12, pp. 30–31 (1998); Cote, G. L., *Diabetes Technology and Therapeutics*, Vol. 1 (1999). The addition of optical modulators to this polarimeter also increases its sensitivity over that previously achieved. A higher sensitivity polarimeter has been suggested by placing the glucose samples (and in an eventual operational system, presumably the eye) under a moderate magnetic field, so as to enhance the polarization rotation due to glucose. Jang, S. et al., Optical Sensor using the Magnetic Optical Rotatory Effect of Glucose, *IEEE LEOS Newsletter*, Vol. 12, pp. 28–30 (1998).

Another approach to the unambiguous measurement of the glucose concentration in the aqueous ocular humor is the use of spectroscopic techniques. U.S. Pat. No. 5,243,983 to Tarr and Steffes discloses the use of stimulated Raman spectroscopy for such measurements, since the cost of components was low, and since glucose-specific features of the Raman spectrum in the aqueous humor could be identified and measured with such a system. Tarr, R. V. et al., The Non-Invasive Blood Glucose Measure of D-Glucose in the Ocular Aqueous Humor using Stimulated Raman Spectroscopy, *IEEE LEOS Newsletter*, Vol. 12, pp. 22–27 (1998). In a stimulated Raman system, two laser waves whose frequencies are separated by a Raman resonance frequency specific to glucose traverse a medium, and the amount of energy which is transferred from one beam to the other (through stimulated Raman scattering) is measured and related to the abundance of glucose.

The spectral nature of the aqueous ocular fluids allows Raman spectroscopy to be highly effective for identifying the concentration of constituent abundances, including glucose. Erckens, R. J. et al., Raman Spectroscopy for Noninvasive Characterization of Ocular Tissue—Potential for Detection of Biological Molecules, *Journal of Raman Spectroscopy*, Vol. 28, pp. 293–299 (1997). One feature of a system employing stimulated Raman spectroscopy is its use of the same transversal path used in the polarimetric systems discussed above. This provides a much lower level of retinal exposure, and allows measurements of glucose concentrations at the level of 0.5% (by weight) using low-cost, low-power, solid-state lasers. Tarr, R. V. et al., The Non-Invasive Blood Glucose Measure of D-Glucose in the Ocular Aqueous Humor using Stimulated Raman Spectroscopy, *IEEE LEOS Newsletter*, Vol. 12, pp. 22–27 (1998). Since the sensitivity of stimulated Raman systems is related to the power and stability of the lasers used, and to the spatial compactness of the laser beams, use of higher stability, higher power semiconductor lasers with more compact and uniform spatial beamwidths could make possible measurements at the 0.01% level over paths comparable to that through the cornea.

Using the more traditional spontaneous Raman spectroscopic technique, successful measurements of the concentration of glucose in a simulated rabbit aqueous humor have been made. Lambert, J. et al., Measurement of Physiologic Glucose Levels Using Raman Spectroscopy in a Rabbit Aqueous Humor Model, *IEEE LEOS Newsletter*, Vol. 12, pp. 19–22 (1998); Lambert, J., *Diabetes Technology and Therapeutics*, Vol. 1 (1999). Likewise in-vitro measurements of the glucose concentration in rabbit aqueous humor samples have been made. Id. While the stimulated Raman technique is often more sensitive since the interference from protein fluorescence is not present, this spontaneous Raman spectroscopic technique can achieve high sensitivity through the incorporation of high-level spectral retrieval techniques to infer glucose concentration based on the entire measured Raman spectrum, rather than just a few key Raman frequencies. Sensitivities better than 50 mg/dl have been made when measuring simulated rabbit aqueous humor. Lambert, J. et al., Measurement of Physiologic Glucose Levels Using Raman Spectroscopy in a Rabbit Aqueous Humor Model, *IEEE LEOS Newsletter*, Vol. 12, pp. 19–22 (1998). Even though spontaneous Raman systems require direct frontal illumination of the aqueous humor to obtain detectable scattering from glucose, focusing occurs within the cornea, which both (beneficially) increases the power density in aqueous humor, and reduces the power density in the vicinity of the retina. Lambert, J., *Diabetes Technology and Therapeutics*, Vol. 1 (1999).

To date, none of these methods has proven to have the reliability, accuracy and ease of use which would optimally be desirable to produce a workable device for everyday patient use. Clearly, there is a need for an improved non-invasive method for obtaining an approximation of a patient's blood glucose level which has increased reliability, accuracy and ease of use.

Accordingly, it is an object of the present invention to provide a process for measuring the blood glucose levels of humans using a non-invasive technique which is convenient and easy to use by patients on their own.

Furthermore, it is an object of the present invention to provide a process for measuring the blood glucose levels of humans which is not subject to path length variability and is thus more accurate than conventional non-invasive methods.

It is yet another object of the present invention to provide a method for measuring the blood glucose levels of humans based upon their ocular refractivity which minimizes the exposure of the retina to potentially damaging power levels of electromagnetic radiation.

BRIEF DESCRIPTION OF THE INVENTION

The above objectives are accomplished according to the present invention by providing a process and method for the non-invasive determination of a mammal's, preferably a human patient's, blood glucose level by measuring the required refractive correction of the mammal's eyes. More specifically, the method of the present invention includes the steps of measuring the mammal's required refractive correction and correlating the measured required refractive correction to the mammal's blood glucose level using a previously determined relationship between the mammal's required refractive correction at a known blood glucose concentration.

Other objects, aspects, and advantages of the present invention will be apparent to those skilled in the art from a reading of the following detailed disclosure of the invention.

BRIEF DESCRIPTION OF THE FIGURES

The construction and design to carry out the invention will hereinafter be described together with other features thereof. The invention will be more readily understood from a reading of the following specification and by reference to the accompanying drawings forming a part thereof, wherein an example of the invention is shown and wherein.

DETAILED DESCRIPTION OF THE PREFERRED EMBODIMENT

Figure 1:
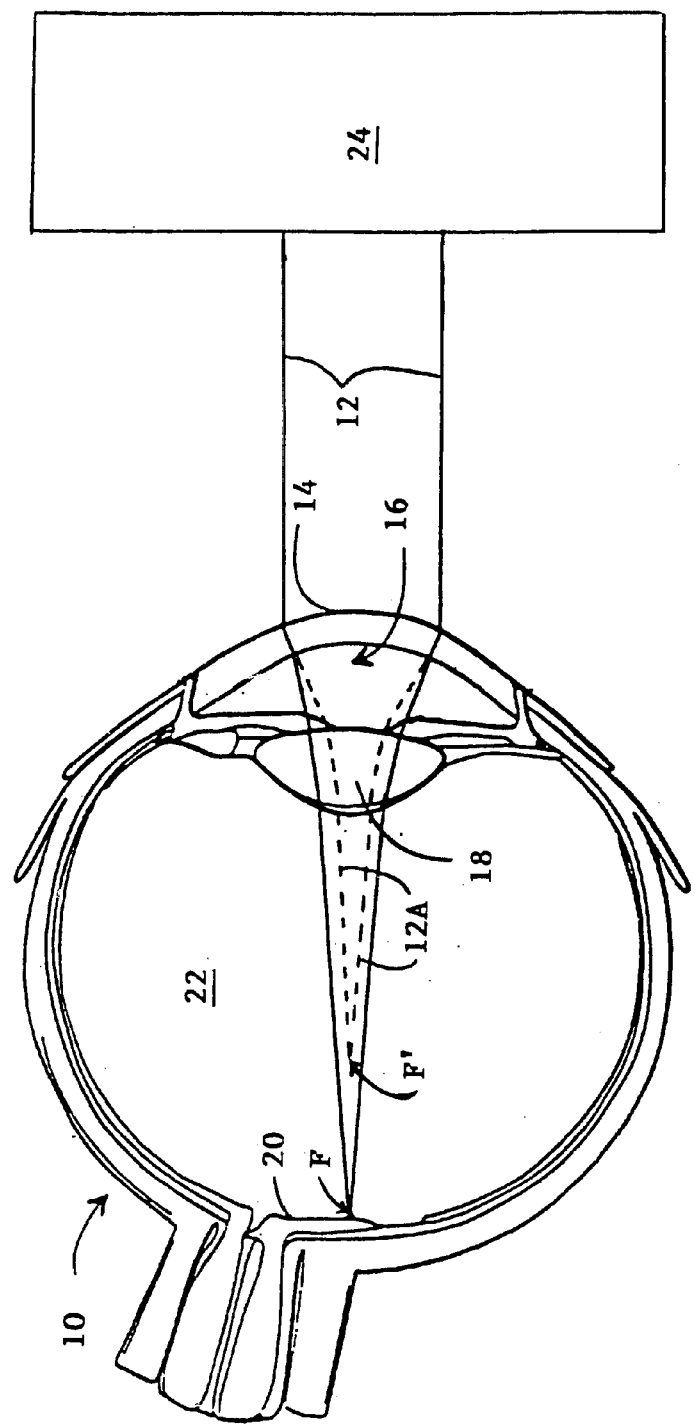
FIG. 1 is a block diagram illustrating a preferred embodiment of the method of the present invention.

Referring now in more detail to the drawings, the invention will now be described in detail. As shown in FIG. 1, the present invention involves the use of a means for measuring the required refractive correction of a mammal's eyes and the correlation of the measured refractive correction to the blood glucose level of the mammal. The preferred mammal is a human patient which will be referred to simply as the patient. The general method for determining the glucose concentration is to compare the current required refractive correction necessary in the patient to the known required refractive correction of a patient who has a known blood glucose concentration, and to compare the difference between the two to a known database of differences, interpolating to determine the patient's blood glucose concentration.

A typical eyeball 10 is shown in FIG. 1. Light rays 12 pass through the cornea 14, the aqueous humor 16, and the lens 18. For eyes that do not need correction, and for eyes that have proper correction (eyeglasses, contact lenses, corrective surgery or the like), the light rays 12 focus on the retina 20 at point F. For eyes that need correction and are not corrected, the light rays 12 do not focus on the retina 20, but either focus at a point inside the interior 22 of the eyeball 10, or at a theoretical point outside of the eyeball 10. This new point can be measured using a measurement device, such as refraction measurement device 24.

For example and not limitation, refraction measurement device 24 may be a traditional lens set or an automatic refractometer. Traditional lens sets are used in conjunction with charts, such as the well-known chart with letters descending in size from the top of the chart to the bottom of the chart. The patient views the chart through the lens set, and various different lenses are placed in front of the patient's eyes. When the patient is able to comfortably read certain lines of the chart, the practitioner notes which lens was used, and this determines the required refractive correction. Automatic refractometers work by projecting an image on the back of the patient's eye and comparing the image on the back of the patient's eye (on the retina) with a computer database. When the image on the back of the patient's eye matches a certain image in the database designated as correct vision, this determines the required refractive correction. One of ordinary skill in the art will recognize that any of the known or yet to be discovered methods of determining the required refractive correction are suitable for use in the present invention.

The aqueous humor 16 has a certain refractive index. This refractive index varies with the blood glucose concentration. Under normal circumstances, the light rays 12 pass through the aqueous humor 16 and are refracted a certain amount. When the blood glucose concentration changes, the refractive index of the aqueous humor 16 changes, thus refracting the light rays 12 to a different path 12A. This causes the light rays 12A to focus at a different point, such as point F'. The difference between point F and point F' is measurable by a refraction measurement device 24. This difference is compared to a known database of correlative values, and the new blood glucose concentration can be determined.

In one preferred embodiment refraction measurement device 24 uses laser light as the light rays 12 to determine the current optical refractivity of the aqueous humor and compare it to a baseline measurement of the aqueous humor. The difference between the current optical refractivity and the baseline refractivity is indicative of the change in the blood glucose concentration of the patient, and the current blood glucose concentration of the patient can be determined without invasion into the body.

The general method for determining the glucose concentration is to compare the current required refractive correction necessary in the patient to the known required refractive correction of the patient at a known blood glucose concentration, and to compare the difference between the two to a known database of correlative differences. For example, a patient has a known required refractive correction of 3.25 diopters and a known blood glucose concentration of 95 mg/dl. The current required refractive correction for the patient is determined by any of the known methods to be 3.75 diopters. The difference of 0.50 diopters is compared to a known database, and the current blood glucose concentration is interpolated.

The database with the relationship among the known refractive correction, the known blood glucose concentration, the current required refractive correction, and the current blood glucose concentration can be developed without undue experimentation by one of ordinary skill in the art. For example, one method would be to measure the normal required refractive correction and the normal blood glucose concentration of a patient, induce a change in the blood glucose concentration of the patient by artificial means (fasting or ingestion of high-glucose foods or liquids), and measuring the current required refractive correction and the current blood glucose concentration of the patient after a predetermined time period from the onset of the artificial means of altering the blood glucose concentration of the patient. A more detailed examination of the relationship between measured refractive correction and blood glucose levels will be presented below in the Theoretical Analysis section.

Figure 2:
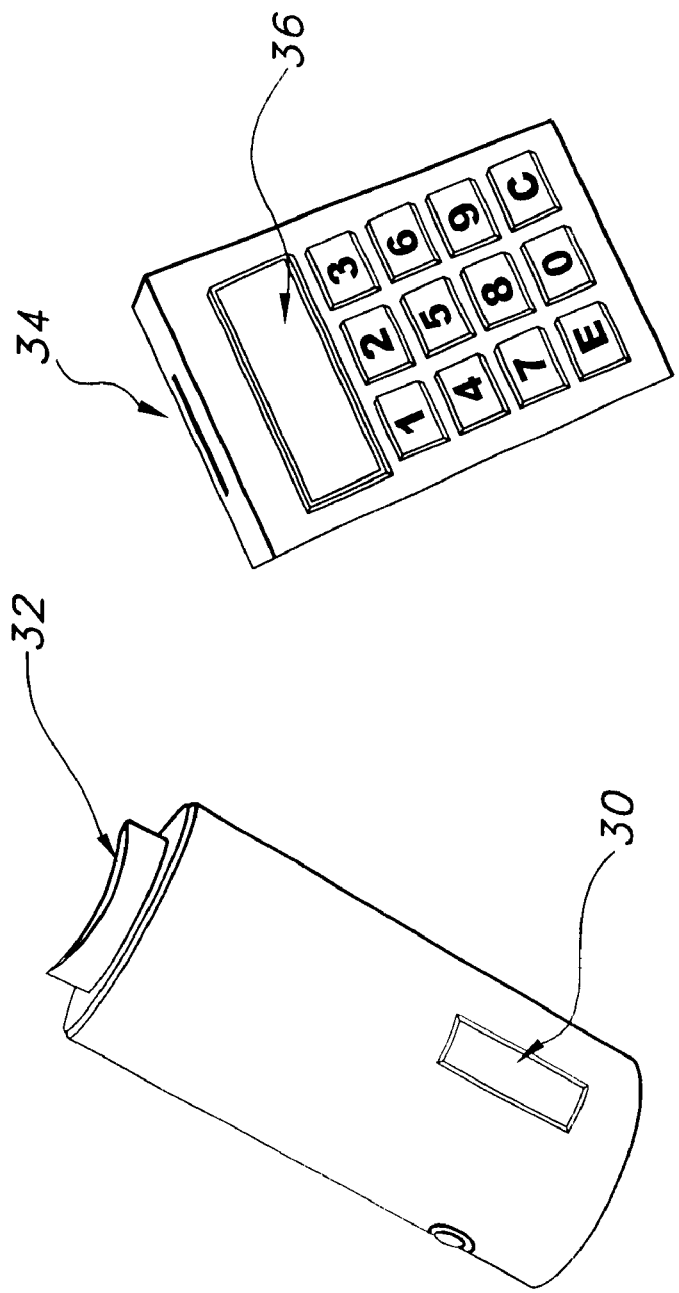
FIG. 2 is perspective view of a portable refractometer and calculator in accordance with a preferred embodiment of the present invention.

In an envisioned preferable embodiment, the refractive correction necessary for the patient's eye will be measured using a small handheld automatic refractor 30 about the size of a binocular, as shown in FIG. 2. One end of the device will have a cup-like aperture 32 that will fit onto the patient's eyes 10 (left or right). The cup-like aperture 32 is designed to prevent the external light sources (light, electrical outlets, electrical appliances) from interfering with accurate measurements. It is envisioned that the automatic refractor 30 will communicate with a handheld microprocessor 34 which will display a numerical blood glucose value (mg/dl) to the patient on an LCD display 36.

Theoretical Analysis

Figure 3:
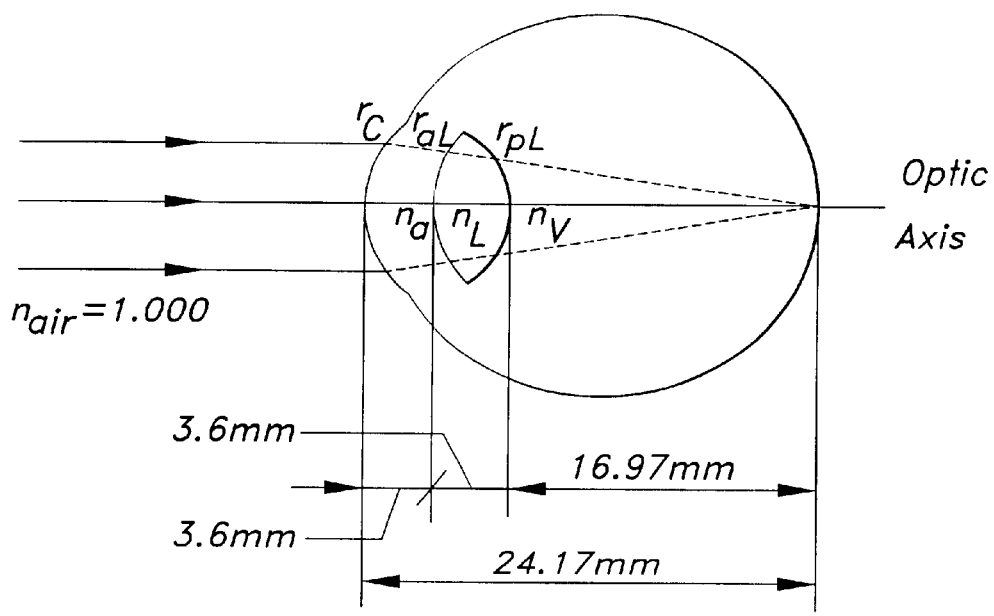
FIG. 3 is a schematic diagram illustrating Gullstrand's Model of the eye.

To implement the method of the present invention, we first determined the relationship between blood glucose level and the refractive index of the eye. The relationship between D-glucose concentration, refractive index, and aqueous solution was calculated. The Gullstrand's theoretical model was used (see FIG. 3). From this figure, collection of following data is obtained: the radius of cornea 14, lens 18 and vitreous body. Utilizing the already established ratio of 1.8 (glucose concentration in blood to the concentration of glucose in aqueous humor 16), calculation for the changes in refractive indices of aqueous humor 16 is shown in the following section (also refer to Table 1).

TABLE 1

| Thickness | |
|---|---|
| Cornea | 0.527 mm |
| Aqueous Humor | 3.07 mm |
| Lens | 3.6 mm |
| Vitreous Humor | 16.97 mm |
| Radius | |
| Cornea | 7.8 mm |
| Anterior Lens Surface | 10 mm |
| Posterior Lens Surface | −6 mm |
| Refractive Index | |
| Cornea | 1.376 |
| Aqueous Humor | Various |
| Lens | 1.413 |
| Vitreous Humor | 1.336 |

First, a table containing the properties of D-glucose in aqueous solution was used to find refractive index change with different glucose concentration in the eye 10. The content composition of aqueous humor 16 (in the human eye) is more complex than pure aqueous solution. Assuming that the glucose concentration (given in the sample calculation of the Gullstrand's model) is at 100 mg/dl, a value of 1.3335795333 was calculated. Given the slope of the linear equation (3.684^−6), and the value of the y-intercept, equation (1) was generated.

$$R = 3.684 * 10^{-6} * G + 1.33366 \qquad (1)$$

R is the refractive index. The variable G is the glucose concentration in aqueous solution. Thus, equation (1) sets forth the relationship between the refractive index and concentration of glucose in eye.

Next, the concentration of glucose in the aqueous humor 16 was obtained by dividing the blood glucose concentration by a factor of 1.8. Using this information, equation (2) was generated.

$$R' = 3.684 * 10^{-6} * G' + 1.3357953 \qquad (2)$$

R' is the refractive index in the aqueous humor 16. The variable G' is the glucose concentration in the eye 10. Equations (1) and (2) were used as a basis for the theoretical calculations.

Two different approaches were used to obtain the necessary data for the theoretical calculations. First, graphical analysis was used. The magnitude of the modeled eye 10 was enlarged by factor of 20. Next, the curvature of cornea 14 and the lens 18 (found in the Gullstrand's model and Snell's law) was used to trace the light ray. However, the hand ray tracing calculations were not accurate in that, for a person with a perfect vision, the graph showed an approximate error of six diopters.

Figure 4:
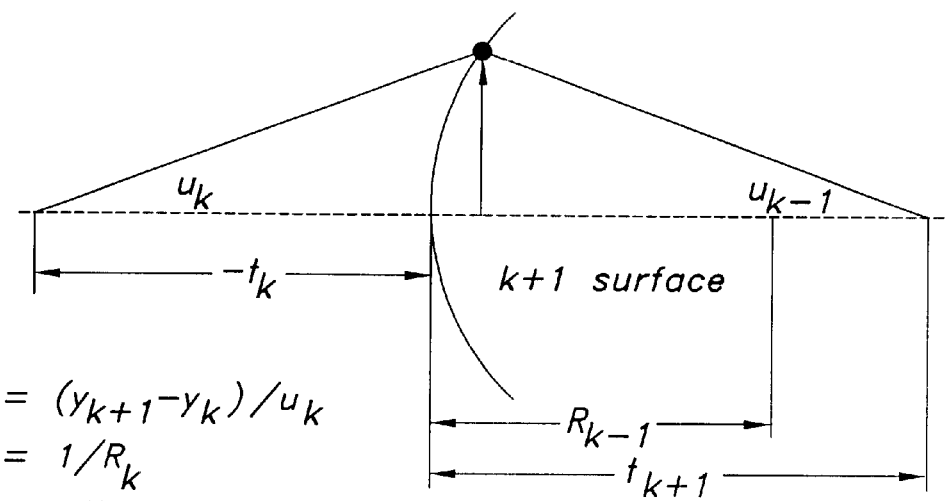
FIG. 4 is a schematic illustrating the Paraxial Ray Tracing technique used in the theoretical calculation of refractive parameters.

Therefore, it was necessary to utilize a second method, Paraxial Ray Tracing, to perform the calculations. Paraxial Ray Tracing is accomplished by tracing the path of a light ray with very small units (mm were used). The Paraxial Ray Tracing method satisfied the design requirements. FIG. 4 is a graphical explanation of the paraxial ray tracing. In this figure, y is the ray height at the surface. The variable u is the slope angle, and t is the distance between two surfaces. The last variable R is the radius of the surface. A diameter of 30 mm was assumed as the incident ray to the eye. Through this assumption, beginning value of y=15 mm was obtained (also assuming a infinite ray source). Table 2 summarizes the results of the mathematical calculations obtained through this example. Table 2 was generated for a patient having a blood glucose concentration within the normal range (72 mg/dl).

TABLE 2

| $t_k$ | ∞ | | 0.529 | | 3.07 | | 3.6 | | 16.89 | |
|---|---|---|---|---|---|---|---|---|---|---|
| $n_k$ | 1 | | 1.376 | | 1.336 | | 1.413 | | 1.336 | |
| $c_k$ | 0 | 1/7.8 | | 1/7.8 | | 1/10 | | −1/6 | | |
| $y_k$ | 1.5 | 1.5 | | 1.4722 | | 1.323 | | 1.323 | | 0 |
| $nu_k$ | 0 | | −0.0723 | | −0.0648 | | −0.0750 | | −0.0895 | |
| $u_k$ | 0 | | −0.0525 | | −0.0485 | | −0.0531 | | −0.0670 | |

Application of these equations yields the following results. For the person with normal blood glucose concentration (calculation shown in Table 2), the focal point is 16.89 mm behind the posterior of the lens. This implies that the distance between the focal point and the retina 20 is −5.3 μm. This is equal to a refractive correction reading of −0.19 diopters. This is very close to perfect vision. Next, another calculation with glucose concentration of 180 mg/dl was performed. Through this calculation, the result of −0.26 diopters was obtained. Using equation (3) with two calculated parameters, blood glucose level was determined.

$$GC = -1408.72 * D - 195.65 \qquad (3)$$

The variable GC is the glucose concentration in blood, and D is the refractive correction. The slope of equation (3) is should remain constant from person to person. The slope is the relationship between glucose concentration and diopters. The constant (195.65) in the equation (3) will vary from person to person. This constant can vary due to factors such as the condition of the patient's eye (nearsighted or farsighted), age, and/or astigmatism. The subject used in Example 1 was nearsighted. In comparing the theoretical versus the experiment results, the analysis need only rely upon the changes in the relative slope of the two equations.

EXAMPLE 1

Of major concern in measurement of ocular glucose for determining plasma glucose levels is the potential for delays in changes in the ocular glucose concentration relative to changes in the plasma glucose (i.e., latency). Kinsey, V. E. et al., Transport of Glucose Across Blood-Aqueous Barriers as Affected by Insulin, *Journal of Physiology*, Vol. 156, pp. 8–16 (1961); DiMattio, J., Decreased Ascorbic Acid Entry into Cornea of Streptozotocin-Diabetic Rats and Guinea Pigs, *Exp. Eye Res.*, Vol. 55, pp. 337–344 (1992). The dynamic relationship between ocular glucose and plasma glucose has shown to be rapid in rabbits and in rats, but time constants for glucose equilibration in humans have not been determined.

Figure 5A:
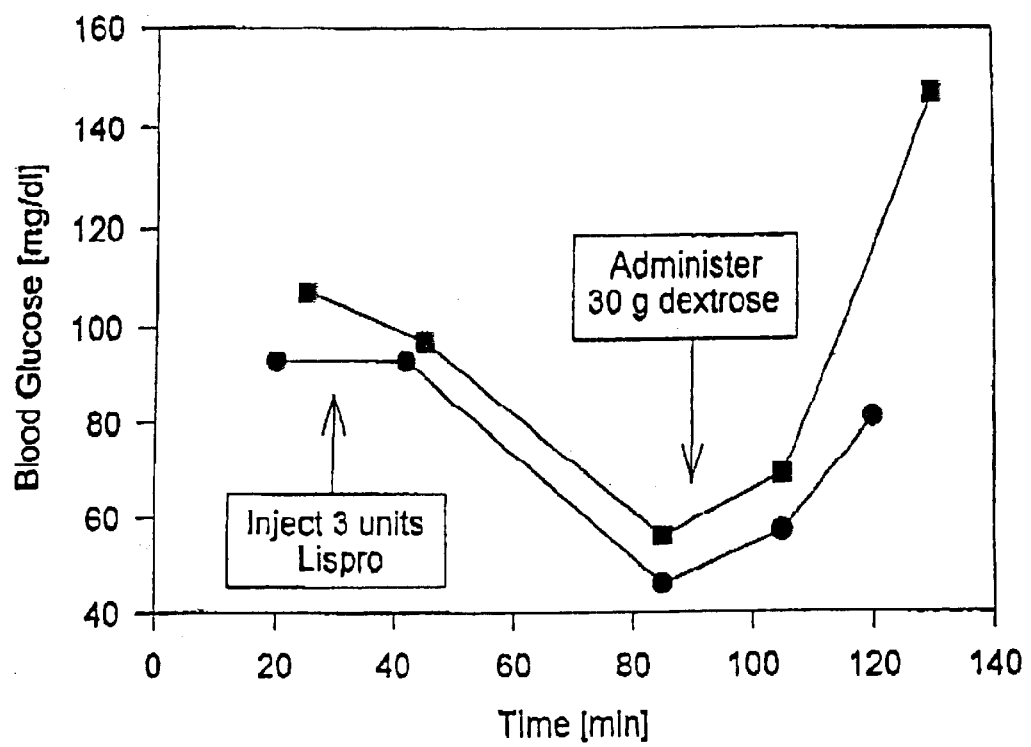
FIG. 5A is a comparison of finger-stick measurements of whole blood glucose taken with One-Touch brand system (circles) and Fast-Take brand system (squares).

To provide some indication of the rapidity of this equilibration, a demonstration was conducted involving a well-controlled IDDM patient (Hb-Alc<6%) regulated with an insulin pump. As shown in FIG. 5A, a baseline whole-blood glucose level of approximately 95 mg/dl was maintained in the fasting patient using an insulin pump administering 0.5 units/hr of Lispro insulin analog. Hypoglycemia was induced with a bolus administration of 3 units Lispro. Concurrent measurement of refractive effects of ocular glucose on the patient's required refractive correction were made by a practitioner using both a Humphries brand auto-refractor and a traditional lens set.

Figure 5B:
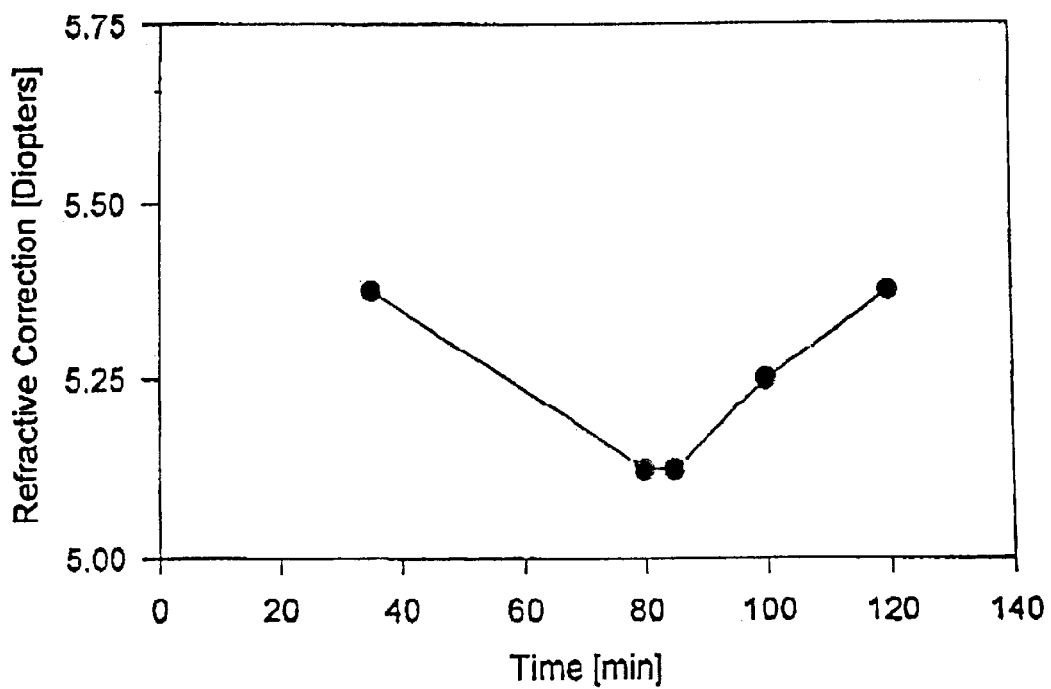
FIG. 5B is the measured required optical refractive correction for a test patient during induced hypoglycemia.

As shown in FIG. 5B, the patient's mean correction (average of both eyes), which was stable at 5.375 diopters previous to the experiment decreased measurably (0.25 diopters) upon induction of hypoglycemia with minimal delay. Its return to the previous stable value tracked that of the digital capillary blood glucose measured using two different meters nearly instantaneously. Obviously, constituents other than glucose have effect on the refractivity of the aqueous humor. However, on a short-term basis, the variability of these constituents is relatively small in an otherwise-healthy patient. Thus, such a refractivity measurement can accurately reflect short-term variations of ocular glucose.

Such a demonstration shows the utility of an instrument which measures ocular glucose in the treatment and control of diabetes. Based on the relative spectral simplicity of the aqueous humor, and the rapidity with which variations in its glucose concentration mirrors that in the blood, laser-based measurement of glucose concentration in the aqueous humor can be used in a system for non-invasive determination of blood glucose levels. Either multi-wavelength polarimetry or Raman spectroscopy can yield a useful instrument for both clinical use and patient self-monitoring. Either technique can also be combined with refractive index measurement.

EXAMPLE 2

The utility of the present invention was demonstrated using a (Type 1) diabetic patient as a test subject. As a control, the patient used a plasma-calibrated blood glucose meter (FastTake™ brand) to determine his blood glucose in the plasma portion of his blood. This means that the red blood cells are removed before the meter determines the blood glucose level. The refraction portion of the testing procedure utilized a Reichert Ophthalmic Instruments Model AR350 auto refractor, which is affordable, easy to operate, and has a high resolution (0.01 D).

Shortly after the blood glucose meter reading (within a 5 minute period), the patient used the AR350 auto refractor to determine his refractive correction in diopters. The auto refractor was preset to take five measurements in one sitting. For every blood glucose reading, there were five measurements taken.

During the course of testing it became apparent that elimination of ambient room lighting could significantly improve the accuracy of the refractivity measurements. In fact, no significant correlation was observed between blood glucose levels and refractive correction at high levels of ambient light. Accordingly, the refractivity measurements should be carried out under conditions having minimal ambient light or using apparatus which shields ambient light away from the patient's eye. This function is provided by the use of a cup like aperture 32 through which the patient looks, as illustrated in FIG. 2

A total of twelve glucose readings were taken with the glucose meter. For each blood glucose reading, five auto refractor measurements were take. A total of sixty data pairs were obtained. Of the auto refractor measurements taken (for each trial), the highest and the lowest values were discarded. For each glucose reading, the remaining three auto refractor measurements were recorded for a total of thirty-six data pairs shown in Table 3. The x-value is the blood glucose level and the y-value is the corresponding refractive correction determined by the auto refractor.

TABLE 3

| Data From Testing | | | | | | | | | | | | | | | | | | |
|---|---|---|---|---|---|---|---|---|---|---|---|---|---|---|---|---|---|---|
| Test: | 1 | 2 | 3 | 4 | 5 | 6 | 7 | 8 | 9 | 10 | 11 | 12 | 13 | 14 | 15 | 16 | 17 | 18 |
| x: | 42 | 42 | 42 | 50 | 50 | 50 | 61 | 61 | 61 | 61 | 61 | 61 | 98 | 98 | 98 | 168 | 168 | 168 |
| y: | −4.92 | −4.94 | −5.04 | −5.01 | −5.09 | −5.07 | −5.04 | −4.97 | −4.99 | −5.09 | −5.14 | −5.11 | −4.84 | −4.91 | −4.98 | −4.91 | −5 | −5.2 |
| Test: | 19 | 20 | 21 | 22 | 23 | 24 | 25 | 26 | 27 | 28 | 29 | 30 | 31 | 32 | 33 | 34 | 35 | 36 |
| x: | 183 | 183 | 183 | 185 | 185 | 185 | 198 | 198 | 198 | 213 | 213 | 213 | 234 | 234 | 234 | 276 | 276 | 276 |
| y: | −5.04 | −5.04 | −5.35 | −5.15 | −5.2 | −5.2 | −5 | −5.02 | −5.16 | −4.92 | −5.04 | −5.17 | −4.99 | −5.12 | −5.32 | −5.39 | −5.09 | −5.38 |

Figure 6:
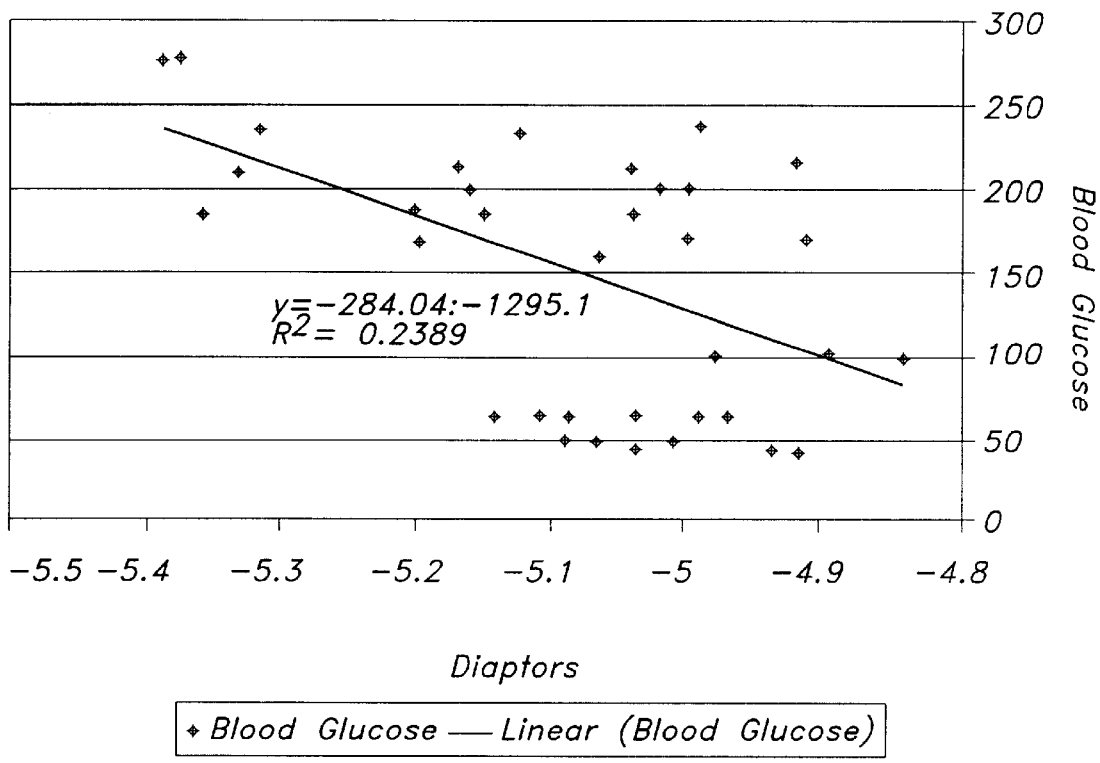
FIG. 6 is a graph of the data of Example 2 illustrating the correlation of blood glucose level with required refractive correction.

FIG. 6 is a graphical display of the data in Table 3. A trend line shows that, as blood glucose increases, the patient becomes more nearsighted. Equation (4), $$y = -284.04x - 1295.1 \quad (4)$$

also shown in the FIG. 6, is the calibrated equation for the patient who was tested (each patient will have his/her own calibration equation). The calibrated equation for each individual should display similar trends.

The correlation between refractive correction and blood glucose was calculated using equation (5).

$$r = \frac{\sum(x_i - \bar{x})(y_i - \bar{y})}{\sqrt{\sum(x_i - \bar{x})^2}\sqrt{\sum(y_i - \bar{y})^2}} = \frac{S_{xy}}{\sqrt{S_{xx}}\sqrt{S_{yy}}} \quad (5)$$

where $$S_{xx} = \sum x_i^2 - \frac{(\sum x_i)^2}{n} \quad (6)$$

$$S_{yy} = \sum y_i^2 - \frac{(\sum y_i)^2}{n} \quad (7)$$

$$S_{xy} = \sum x_i y_i - \frac{(\sum x_i)(\sum y_i)}{n}. \quad (8)$$

Pearson's sample correlation r=−0.48867 and an r²=0.2389 was generated. This r-value does imply that there is a weak correlation. A perfect linear relationship would be r=(+/−)1.

From the result of the theoretical calculations, the relationship between the glucose concentration and the refractive correction had a slope of −1408.72. The experimental slope is −284.04. Percent error in this case (of the two slopes) is [1-(experimental/theoretical)]=79.83%. Nonetheless, the relationship between glucose concentration of the eye and blood glucose is visible, demonstrating the utility of this technique.

It, thus, will be appreciated that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. A method for determining a mammal's blood glucose level based on ocular refractive correction, said method comprising the steps of:

measuring the ocular refractive correction of the mammal;

relating the measured ocular refractive correction of the mammal to the mammal's blood glucose level by comparing the measured ocular refractive correction to a database of known ocular refractive corrections and blood glucose concentrations.

2. The method of claim 1, wherein the mammal is a human.

3. The method of claim 2, including the further steps of:

measuring the ocular refractive correction at least a second time; and averaging the measured ocular refractive corrections to obtain a value.

4. The method of claim 2, wherein said step of measuring the ocular refractive correction is performed using a traditional lens set.

5. The method of claim 2, wherein said step of measuring the ocular refractive correction is performed using an automatic refractometer.

6. The method of claim 2, further including the initial step of measuring the ocular refractive correction at a plurality of known blood glucose levels.

7. The method of claim 2, further including the step of interpolating a blood glucose value correlated to the measured ocular refractive correction in relation to a plurality of data from said database.

8. The method of claim 2, wherein said measuring step includes the step of shielding an eye from external light.

9. An apparatus for determining a mammal's blood glucose level, said apparatus comprising:

a refractometer for measuring ocular refractive correction, said refractometer outputting data indicative of the ocular refractive correction; and a processor adapted to receive said data indicative of the ocular refractive correction from said refractometer, said processor being operative to correlate said data to a correlated blood glucose level, said processor outputting a signal indicative of said correlated blood glucose level.

10. The apparatus of claim 9, wherein the mammal is a human.

11. The apparatus of claim 10, further comprising a display adapted to display the correlated blood glucose level.

12. A method for determining blood glucose concentrations based on ocular refractive correction, said method comprising the steps of:

measuring the ocular refractive correction needed to correct a mammal's vision; and comparing the ocular refractive correction with predetermined ocular refractive corrections correlated to predetermined blood glucose concentrations.

13. The method of claim 12, wherein the ocular refractive correction is measured with an automatic refractometer.

14. The method of claim 13, wherein the mammal is human.

15. The method of claim 12, wherein the ocular refractive correction is measured in diopters.

16. A method of monitoring changes in blood glucose concentration, said method comprising the steps of:

calibrating a patient's blood glucose concentration with the patient's ocular refractive correction;

measuring the patient's ocular refractive correction; and interpolating the patient's blood glucose concentration based on the calibration.

17. A method of monitoring changes in blood glucose concentration, said method comprising the steps of:

taking a first ocular refractive correction measurement of a patient;

taking a first blood glucose concentration measurement from the patient;

taking a second ocular refractive correction measurement and a second blood glucose measurement from the patient after inducing a change in the patient's blood glucose concentration;

correlating the ocular refractive correction measurements with the corresponding blood glucose concentrations;

taking a third ocular refractive correction measurement of the patient; and interpolating the blood glucose concentration corresponding to the third ocular refractive correction measurement.

* * * * *